US008728127B2

(12) United States Patent
Stewart

(10) Patent No.: US 8,728,127 B2
(45) Date of Patent: May 20, 2014

(54) BONE PLATE INCORPORATING A COMPRESSION MECHANISM AND ASSOCIATED SURGICAL METHODS

(75) Inventor: Geoffrey Stewart, Orlando, FL (US)

(73) Assignee: Spineworks, LLC, Orlando, FL (US)

( * ) Notice: Subject to any disclaimer, the term of this patent is extended or adjusted under 35 U.S.C. 154(b) by 159 days.

(21) Appl. No.: 13/352,130

(22) Filed: Jan. 17, 2012

(65) Prior Publication Data
US 2012/0185000 A1     Jul. 19, 2012

Related U.S. Application Data

(60) Provisional application No. 61/433,736, filed on Jan. 18, 2011.

(51) Int. Cl.
*A61B 17/66*     (2006.01)

(52) U.S. Cl.
USPC .......................................... 606/282; 606/105

(58) Field of Classification Search
USPC ............................................ 606/282, 71, 105
See application file for complete search history.

(56) References Cited

U.S. PATENT DOCUMENTS

| 6,280,445 B1 * | 8/2001 | Morrison et al. ............. 606/292 |
| 2005/0010227 A1 * | 1/2005 | Paul ................................ 606/71 |
| 2008/0234680 A1 * | 9/2008 | Zaiser et al. ..................... 606/71 |

* cited by examiner

*Primary Examiner* — Andrew Yang
(74) *Attorney, Agent, or Firm* — Clements Bernard PLLC; Christopher L. Bernard; Lawrence A. Baratta, Jr.

(57) ABSTRACT

The present invention provides a bone plate that includes a sliding mechanism that allows for both static and dynamic loading and the associated stabilization or partial or whole immobilization of two or more adjacent bone fragments or vertebral bodies of the spine. This sliding mechanism is designed such that as bone resorbs or the like, the sliding mechanism maintains axial compression in a collinear manner across the bone segments.

18 Claims, 4 Drawing Sheets

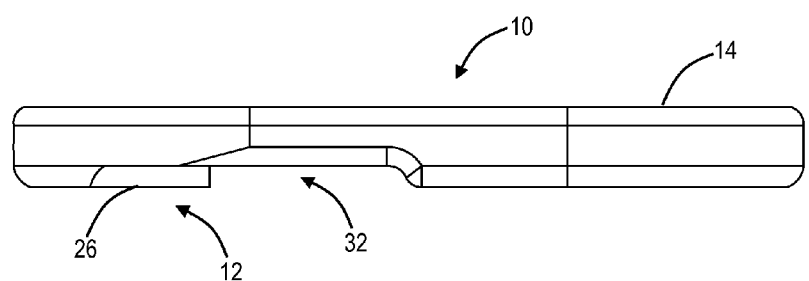
FIG. 1
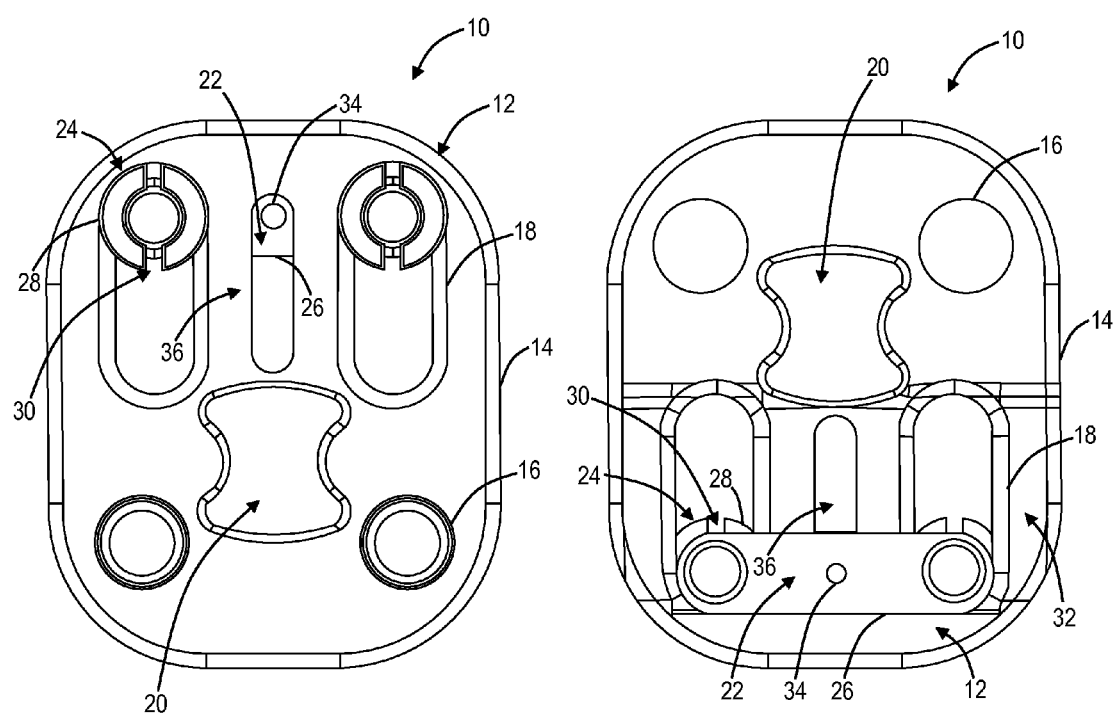
FIG. 2     FIG. 3

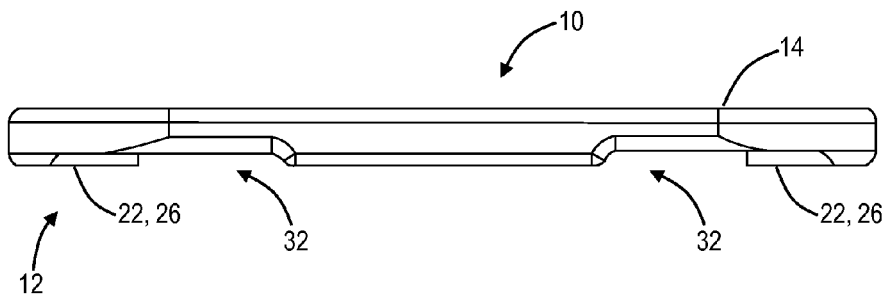
*FIG. 6*
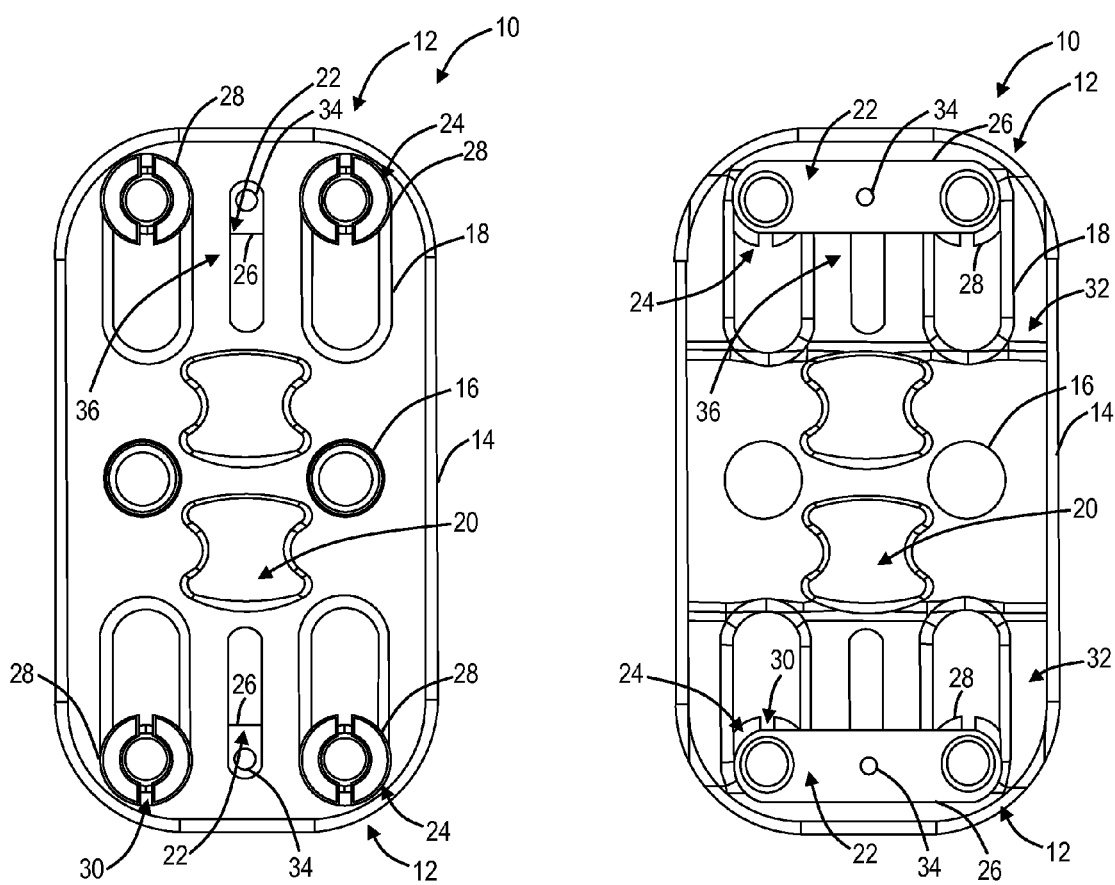
*FIG. 7*          *FIG. 8*

BONE PLATE INCORPORATING A COMPRESSION MECHANISM AND ASSOCIATED SURGICAL METHODS

CROSS-REFERENCE TO RELATED APPLICATION

The present patent application/patent claims the benefit of priority of U.S. Provisional Patent Application No. 61/433,736, filed on Jan. 18, 2011, and entitled "BONE PLATE INCORPORATING A STATIC/DYNAMIC COMPRESSION MECHANISM AND ASSOCIATED SURGICAL METHODS," the contents of which are incorporated in full by reference herein.

FIELD OF THE INVENTION

The present invention relates generally to bone plates for stabilizing and partially or wholly immobilizing bone fragments, adjacent vertebrae, or the like while providing the application of constant static compression intra-operatively and constant static or dynamic compression post-operatively.

BACKGROUND OF THE INVENTION

In the treatment of various orthopedic and spinal ailments and defects, it is desirable to stabilize or partially or wholly immobilize two or more bony segments, with bone arthrodesis or fusion being the desired outcome. By applying compressive force across the site, bone growth is enhanced according to Wolff's law. This is believed to decrease healing time and increase fusion quality.

Similarly, in the treatment of fractures and other orthopedic conditions, stabilizing or immobilizing devices are often placed on bone fragments to maintain bony alignment and impart stability to promote healing. Healing can be further promoted by creating compression across the fracture site intra-operatively and, ideally, allowing dynamic compression across the fracture site post-operatively.

Specifically, spinal fusion is one example of a surgical procedure that is used to stabilize or immobilize adjacent vertebrae in the treatment of an injury or degenerative condition. During the procedure, the intervertebral disc is removed and the intervertebral space is filled with bone graft material and/or a fusion cage. A bone plate is typically used to provide stability to the affected spinal segment, keeping the bone graft material and/or fusion cage in place and providing rigidity.

Often, however, the bone graft material or the bony fragments exhibit bone resorption, which is the process of osteoclasts breaking down the bone and releasing minerals into the bloodstream. As the bone graft material resorbs, there is a loss of contact with the host bone and less compression of the bone graft material, leading to progressively less likelihood of incorporation and healing of the fusion. This process is usually the result of a lack of stimulus for bone maintenance, i.e. compression. This also leads to an exponentially increased load on the bone plate, resulting in an increased occurrence of failed implants, which typically requires revision surgery and means longer recovery times for patients.

The use of a bone plate that allows for dynamic compression post-operatively would enhance the bone arthrodesis process. Dynamic compression would stimulate the healing of the bone graft material to the host bone, resulting in a more rapid and solid fusion. In the case where the bone graft material undergoes resorption or a fusion cage is compromised, dynamic compression would allow for the vertebral column to shift axially, thus promoting the maintenance of bony contact and compression stimulus at the arthrodesis site. In a worst case where the bone graft material completely resorbs and adjacent host bones are then touching, compression stimulus is still applied and arthrodesis can still take place, thereby imparting spinal stability.

BRIEF SUMMARY OF THE INVENTION

In various exemplary embodiments, the present invention provides a bone plate that includes a sliding mechanism that allows for both static and dynamic loading and the associated stabilization or partial or whole immobilization of two or more adjacent bone fragments or vertebral bodies of the spine. This sliding mechanism is designed such that as bone resorbs or the like, the sliding mechanism maintains axial compression in a collinear manner across the bone segments.

In one exemplary embodiment, the present invention provides a bone plate incorporating a compression mechanism, including: a plate structure defining a plurality of screw receiving plate holes and a plurality of screw receiving plate slots; and a carriage assembly engaging the plurality of screw receiving plate slots, wherein the carriage assembly translates axially with respect to the plate structure via the plurality of screw receiving plate slots, thereby providing the compression mechanism. The plurality of screw receiving plate holes receive and retain a plurality of screws that pass through the plate structure and into a first bony structure disposed beneath the plate structure, thereby securing the plate structure to the first bony structure. The carriage assembly includes a plurality of screw receiving carriage assembly stems and an elongate member that joins the plurality of screw receiving carriage assembly stems. The plurality of screw receiving carriage assembly stems receive and retain a plurality of screws that pass through the carriage assembly and into a second bony structure disposed beneath the carriage assembly, thereby securing the carriage assembly to the second bony structure. The plurality of screw receiving plate slots translatably receive the plurality of screw receiving carriage assembly stems. The plurality of screw receiving carriage assembly stems are axially translated with respect to the plate structure in unison and in parallel with respect to one another. The plurality of screw receiving carriage assembly stems prevent rotation of the carriage assembly with respect to the plate structure when the carriage assembly is translated with respect to the plate structure. The carriage assembly translates axially with respect to the plate structure, thereby changing the relative position of a plurality of screws associated with the plate structure and a plurality of screws associated with the carriage assembly, without changing the axial length of the bone plate. The bone plate provides for axial translation of a first bony structure secured to the plate structure with respect to a second bony structure secured to the carriage assembly in a laterally and rotationally constrained manner. The bone plate provides dynamic compression between a first bony structure secured to the plate structure and a second bony structure secured to the carriage assembly.

In another exemplary embodiment, the present invention provides a bone plate incorporating a compression mechanism, including: a plate structure defining a plurality of screw receiving plate holes and a plurality of screw receiving plate slots; and a carriage assembly engaging the plurality of screw receiving plate slots, wherein the carriage assembly translates axially with respect to the plate structure via the plurality of screw receiving plate slots, thereby providing the compression mechanism; wherein the plate structure is secured to a first bony structure using a plurality of screws; wherein the carriage assembly is secured to a second bony structure using a plurality of screws; and wherein the engagement of the plate structure and the carriage assembly provides dynamic compression between the first bony structure and the second bony structure. The plurality of screw receiving plate holes receive and retain the plurality of screws that pass through the plate structure and into the first bony structure disposed beneath the plate structure, thereby securing the plate structure to the first bony structure. The carriage assembly includes a plurality of screw receiving carriage assembly stems and an elongate member that joins the plurality of screw receiving carriage assembly stems. The plurality of screw receiving carriage assembly stems receive and retain the plurality of screws that pass through the carriage assembly and into the second bony structure disposed beneath the carriage assembly, thereby securing the carriage assembly to the second bony structure. The plurality of screw receiving plate slots translatably receive the plurality of screw receiving carriage assembly stems. The plurality of screw receiving carriage assembly stems are axially translated with respect to the plate structure in unison and in parallel with respect to one another. The plurality of screw receiving carriage assembly stems prevent rotation of the carriage assembly with respect to the plate structure when the carriage assembly is translated with respect to the plate structure. The carriage assembly translates axially with respect to the plate structure, thereby changing the relative position of the plurality of screws associated with the plate structure and the plurality of screws associated with the carriage assembly, without changing the axial length of the bone plate. The bone plate provides for axial translation of the first bony structure secured to the plate structure with respect to the second bony structure secured to the carriage assembly in a laterally and rotationally constrained manner.

In a further exemplary embodiment, the present invention provides a bone plate incorporating a compression mechanism, including: a plate structure defining a plurality of screw receiving plate holes and a plurality of screw receiving plate slots; and a carriage assembly engaging the plurality of screw receiving plate slots, wherein the carriage assembly translates axially with respect to the plate structure via the plurality of screw receiving plate slots, thereby providing the compression mechanism; wherein the plate structure is secured to a first bony structure using a plurality of screws; wherein the carriage assembly is secured to a second bony structure using a plurality of screws; and wherein the carriage assembly is locked to the plate structure during implantation. The carriage assembly is subsequently unlocked from the plate structure subsequent to implantation to provide dynamic compression between the first bony structure and the second bony structure. Optionally, the carriage assembly is subsequently locked to the plate structure subsequent to implantation after a compressive load is applied between the carriage assembly and the plate structure to provide static compression between the first bony structure and the second bony structure. The bone plate is implanted through one of an open surgical procedure and a percutaneous surgical procedure, and in one of a single level, double level, and multiple level configuration.

BRIEF DESCRIPTION OF THE DRAWINGS

The present invention is illustrated and described herein with reference to the various drawings, in which like reference numbers are used to denote like device components/method steps, as appropriate, and in which:

FIG. 1 is a planar side view illustrating one exemplary embodiment of a single level bone plate of the present invention;

FIG. 2 is a planar front view illustrating the single level bone plate of FIG. 1;

FIG. 3 is a planar back view illustrating the single level bone plate of FIGS. 1 and 2;

FIG. 6 is a planar side view illustrating one exemplary embodiment of a double level bone plate of the present invention;

FIG. 7 is a planar front view illustrating the double level bone plate of FIG. 6;

FIG. 8 is a planar back view illustrating the double level bone plate of FIGS. 6 and 7.

DETAILED DESCRIPTION OF THE INVENTION

Figure 4:
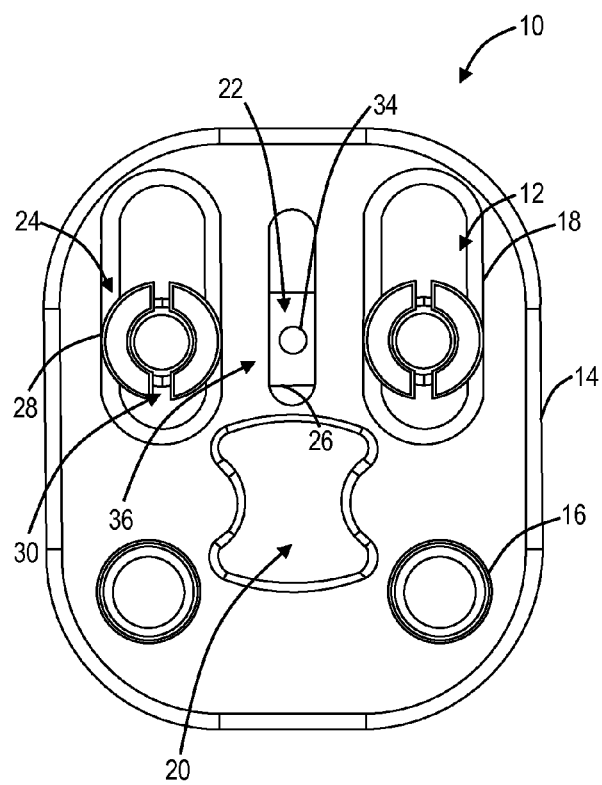
FIG. 4 is another planar front view illustrating the single level bone plate of FIGS. 1-3, highlighting translation of the carriage assembly.
Figure 5:
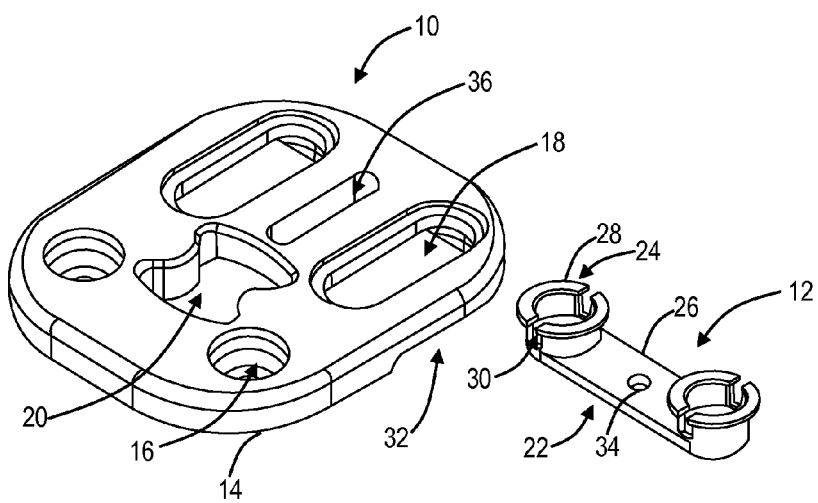
FIG. 5 is a disassembled perspective view illustrating the single level bone plate of FIGS. 1-4.

Referring now to FIGS. 1-5, in one exemplary (single level) embodiment, the bone plate 10 incorporating a compression mechanism 12 includes a plate structure 14 defining a plurality of screw receiving plate holes 16 and a plurality of screw receiving plate slots 18. The plate structure 14 has an overall axial length of between about 20 mm and about 36 mm, an overall lateral width of between about 20 mm and about 30 mm, and an overall thickness of between about 1.8 mm and about 3 mm, although other suitable dimensions can be utilized. As used herein, the term "axial" refers to the direction along the bone fragments or bony structures (i.e. fractured bone or vertebrae) to be joined and the term "lateral" refers to the direction that is substantially perpendicular to the "axial" direction. The plate structure 14 has a generally square or rectangular shape with rounded corners and edges, although other suitable shapes can be utilized. The plate structure 14 can be made of titanium, cobalt chrome, or another alloy, although other suitable surgically implantable materials can be utilized. The plurality of holes 16 are each formed through the plate 14 and sized to receive a conventional bone screw or the like, having a locking head or otherwise. Preferably, the plurality of holes 16 each include a conventional screw retention mechanism, such as a lip, c-ring, petal structure, retention plate, or the like, suitable for retaining the bone screws once in place and preventing them from backing out. Upon implantation, the bone screws are disposed through the holes 16 and into an underlying bony structure, thereby securing the plate 14 to the bony structure. In the non-limiting exemplary embodiment illustrated, two holes 16 are provided. The plate 14 can include any number of additional holes 16, 20 that are desirable as a matter of design choice.

The bone plate 10 also includes a carriage assembly 22 that engages the plurality of screw receiving plate slots 18. The plurality of slots 18 are each formed through the plate 14 and have an axial length of between about 4 mm and about 8 mm, although other suitable dimensions can be utilized. The carriage assembly 22 includes a plurality of screw receiving stems 24 that are joined by an elongate bridge member 26. The stems 24 (a pair of which are illustrated in this non-limiting exemplary embodiment) each include a pair of semi-circular arcuate members 28 that are separated by opposed notches 30. The stems 24 are each sized to receive a conventional bone screw or the like, having a locking head or otherwise. Preferably, the stems 24 each include a conventional screw retention mechanism, such as a lip, c-ring, petal structure, retention plate, or the like, suitable for retaining the bone screws once in place and preventing them from backing out. Upon implantation, the bone screws are disposed through the stems 24 and into an underlying bony structure, thereby securing the carriage assembly 22 to the bony structure. In the non-limiting exemplary embodiment illustrated, the stems 24 are disposed through the slots 18 from the bottom of the plate 14, with the bridge member 26 fitting in a recess manufactured into the bottom of the plate 14. It will be readily apparent to those of ordinary skill in the art, however, that the stems 24 could be disposed through the slots 18 from the top of the plate 14, with the bridge member 26 fitting in a recess manufactured into the top of the plate 14, or the stems 24 could be disposed through the slots 18 from inside the plate 14, with the bridge member 26 fitting in a recess manufactured into the interior of the plate 14. Optionally, the screws inserted into the stems 24 are configured to bias the arcuate members 28 outwards such that they impinge on the sides of the slots 18 to a predetermined degree, thereby providing some resistance of the stems 24 to translation within the slots 18. Further, the bridge member 26 includes a port or screw hole 34 that selectively receives a tool for setting the initial compression provided by the bone plate 10 and/or a screw that rigidly secures the bridge member 26 to the plate 14 (via an additional plate slot 36 or the like), such as intra-operatively or post-operatively, depending upon the preference of the surgeon employing the device.

The carriage assembly 22 translates axially with respect to the plate structure 14 via the plurality of screw receiving plate slots 18, thereby providing the compression mechanism 12. The plurality of screw receiving plate holes 16 receive and retain a plurality of screws that pass through the plate structure 14 and into a first bony structure disposed beneath the plate structure 14, thereby securing the plate structure 14 to the first bony structure. The carriage assembly 22 includes a plurality of screw receiving carriage assembly stems 24 and an elongate member 26 that joins the plurality of screw receiving carriage assembly stems 24. The plurality of screw receiving carriage assembly stems 24 receive and retain a plurality of screws that pass through the carriage assembly 22 and into a second bony structure disposed beneath the carriage assembly 22, thereby securing the carriage assembly 22 to the second bony structure. The carriage assembly 22 may also include additional holes for receiving screws, as desired. The plurality of screw receiving plate slots 18 translatably receive the plurality of screw receiving carriage assembly stems 24. The plurality of screw receiving carriage assembly stems 24 are axially translated with respect to the plate structure 14 in unison, in a collinear manner, and in parallel with respect to one another. The plurality of screw receiving carriage assembly stems 24 prevent rotation of the carriage assembly 22 with respect to the plate structure 14 when the carriage assembly 22 is translated with respect to the plate structure 14. The carriage assembly 22 translates axially with respect to the plate structure 14, thereby changing the relative position of the plurality of screws associated with the plate structure 14 and the plurality of screws associated with the carriage assembly 22, without changing the axial length of the bone plate 10. The bone plate 10 provides for axial translation of a first bony structure secured to the plate structure 14 with respect to a second bony structure secured to the carriage assembly 22 in a laterally and rotationally constrained manner. Thus, the bone plate 10 provides dynamic compression between the first bony structure secured to the plate structure 14 and the second bony structure secured to the carriage assembly 22.

In effect, the bone plate 10 of the present invention provides multiple levels of screws that are secured to bony fragments or structures that are to be joined. These levels of screws are axially translatable with respect to one another, without varying the axial length of the bone plate 10. This provides contact maintenance and dynamic compression between the bony fragments or structures as resorption occurs, etc., thereby promoting fusion at the arthrodesis site.

Referring now to FIGS. 6-8, in another exemplary (double level) embodiment, the bone plate 10 incorporating a compression mechanism 12 includes a plate structure 14 defining a plurality of screw receiving plate holes 16 and a plurality of screw receiving plate slots 18. The plate structure 14 has an overall axial length of between about 34 mm and about 54 mm, an overall lateral width of between about 20 mm and about 30 mm, and an overall thickness of between about 1.8 mm and about 3 mm, although other suitable dimensions can be utilized. As used herein, the term "axial" refers to the direction along the bone fragments or bony structures (i.e. fractured bone or vertebrae) to be joined and the term "lateral" refers to the direction that is substantially perpendicular to the "axial" direction. The plate structure 14 has a generally rectangular shape with rounded corners and edges, although other suitable shapes can be utilized. The plate structure 14 can be made of titanium, cobalt chrome, or another alloy, although other suitable surgically implantable materials can be utilized. The plurality of holes 16 are each formed through the plate 14 and sized to receive a conventional bone screw or the like, having a locking head or otherwise. Preferably, the plurality of holes 16 each include a conventional screw retention mechanism, such as a lip, c-ring, petal structure, retention plate, or the like, suitable for retaining the bone screws once in place and preventing them from backing out. Upon implantation, the bone screws are disposed through the holes 16 and into an underlying bony structure, thereby securing the plate 14 to the bony structure. In the non-limiting exemplary embodiment illustrated, two holes 16 are provided. The plate 14 can include any number of additional holes 16, 20 that are desirable as a matter of design choice.

The bone plate 10 also includes a pair of carriage assemblies 22 that engage the plurality of screw receiving plate slots 18. The plurality of slots 18 are each formed through the plate 14 and have an axial length of between about 4 mm and about 8 mm, although other suitable dimensions can be utilized. Each carriage assembly 22 includes a plurality of screw receiving stems 24 that are joined by an elongate bridge member 26. The stems 24 (a pair of which are illustrated for each carriage assembly 22 in this non-limiting exemplary embodiment) each include a pair of semicircular arcuate members 28 that are separated by opposed notches 30. The stems 24 are each sized to receive a conventional bone screw or the like, having a locking head or otherwise. Preferably, the stems 24 each include a conventional screw retention mechanism, such as a lip, c-ring, petal structure, retention plate, or the like, suitable for retaining the bone screws once in place and preventing them from backing out. Upon implantation, the bone screws are disposed through the stems 24 and into underlying bony structures, thereby securing the carriage assemblies 22 to the bony structures. In the non-limiting exemplary embodiment illustrated, the stems 24 are disposed through the slots 18 from the bottom of the plate 14, with the bridge members 26 fitting in recesses manufactured into the bottom of the plate 14. It will be readily apparent to those of ordinary skill in the art, however, that the stems 24 could be disposed through the slots 18 from the top of the plate 14, with the bridge members 26 fitting in recesses manufactured into the top of the plate 14, or the stems 24 could be disposed through the slots 18 from inside the plate 14, with the bridge members 26 fitting in recesses manufactured into the interior of the plate 14. Optionally, the screws inserted into the stems 24 are configured to bias the arcuate members 28 outwards such that they impinge on the sides of the slots 18 to a predetermined degree, thereby providing some resistance of the stems 24 to translation within the slots 18. Further, the bridge members 26 each include a port or screw hole 34 that selectively receives a tool for setting the initial compression provided by the bone plate 10 and/or screws that rigidly secures the bridge members 26 (one or both) to the plate 14 (via an additional plate slot 36 or the like), such as intra-operatively or post-operatively, depending upon the preference of the surgeon employing the device.

The carriage assemblies 22 translate axially with respect to the plate structure 14 via the plurality of screw receiving plate slots 18, thereby providing the compression mechanism 12. The plurality of screw receiving plate holes 16 receive and retain a plurality of screws that pass through the plate structure 14 and into a first bony structure disposed beneath the plate structure 14, thereby securing the plate structure 14 to the first bony structure. The carriage assemblies 22 include a plurality of screw receiving carriage assembly stems 24 and elongate members 26 that join the plurality of screw receiving carriage assembly stems 24. The plurality of screw receiving carriage assembly stems 24 receive and retain a plurality of screws that pass through the carriage assemblies 22 and into second and third bony structures disposed beneath the carriage assemblies 22, respectively, thereby securing the carriage assemblies 22 to the second and third bony structures. The carriage assemblies 22 may also include additional holes for receiving screws, as desired. The plurality of screw receiving plate slots 18 translatably receive the plurality of screw receiving carriage assembly stems 24. The plurality of screw receiving carriage assembly stems 24 are axially translated with respect to the plate structure 14, in pairs, for example, and in unison, in a collinear manner, and in parallel with respect to one another. The plurality of screw receiving carriage assembly stems 24 prevent rotation of the carriage assembly 22 with respect to the plate structure 14 when the carriage assemblies 22 are translated with respect to the plate structure 14. The carriage assemblies 22 translate axially with respect to the plate structure 14, thereby changing the relative position of the plurality of screws associated with the plate structure 14 and the plurality of screws associated with the carriage assemblies 22, without changing the axial length of the bone plate 10. The bone plate 10 provides for axial translation of a first bony structure secured to the plate structure 14 with respect to second and third bony structures secured to the carriage assemblies 22 in a laterally and rotationally constrained manner. Thus, the bone plate 10 provides dynamic compression between the first bony structure secured to the plate structure 14 and the second and third bony structures secured to the carriage assemblies 22. It will be readily apparent to those of ordinary skill in the art that these concepts can be extended to multiple level embodiments as well. The double level embodiment and these multiple level embodiments are especially useful in spinal applications. It should be noted that pins or other attachment mechanisms can be substituted for screws in all embodiments.

Again, in effect, the bone plate 10 of the present invention provides multiple levels of screws that are secured to bony fragments or structures that are to be joined. These levels of screws are axially translatable with respect to one another, without varying the axial length of the bone plate 10. This provides contact maintenance and dynamic compression between the bony fragments or structures as resorption occurs, etc., thereby promoting fusion at the arthrodesis site.

As an alternative to the above embodiments, the slots 18/bridge member 26 of the present invention may be asymmetric and/or the various screw holes 16,18/screws may be asymmetric/independently locking such that asymmetric compression may be applied by the bone plate 10, for example if a fusion cage and/or bone graft is asymmetric.

Figure 9:
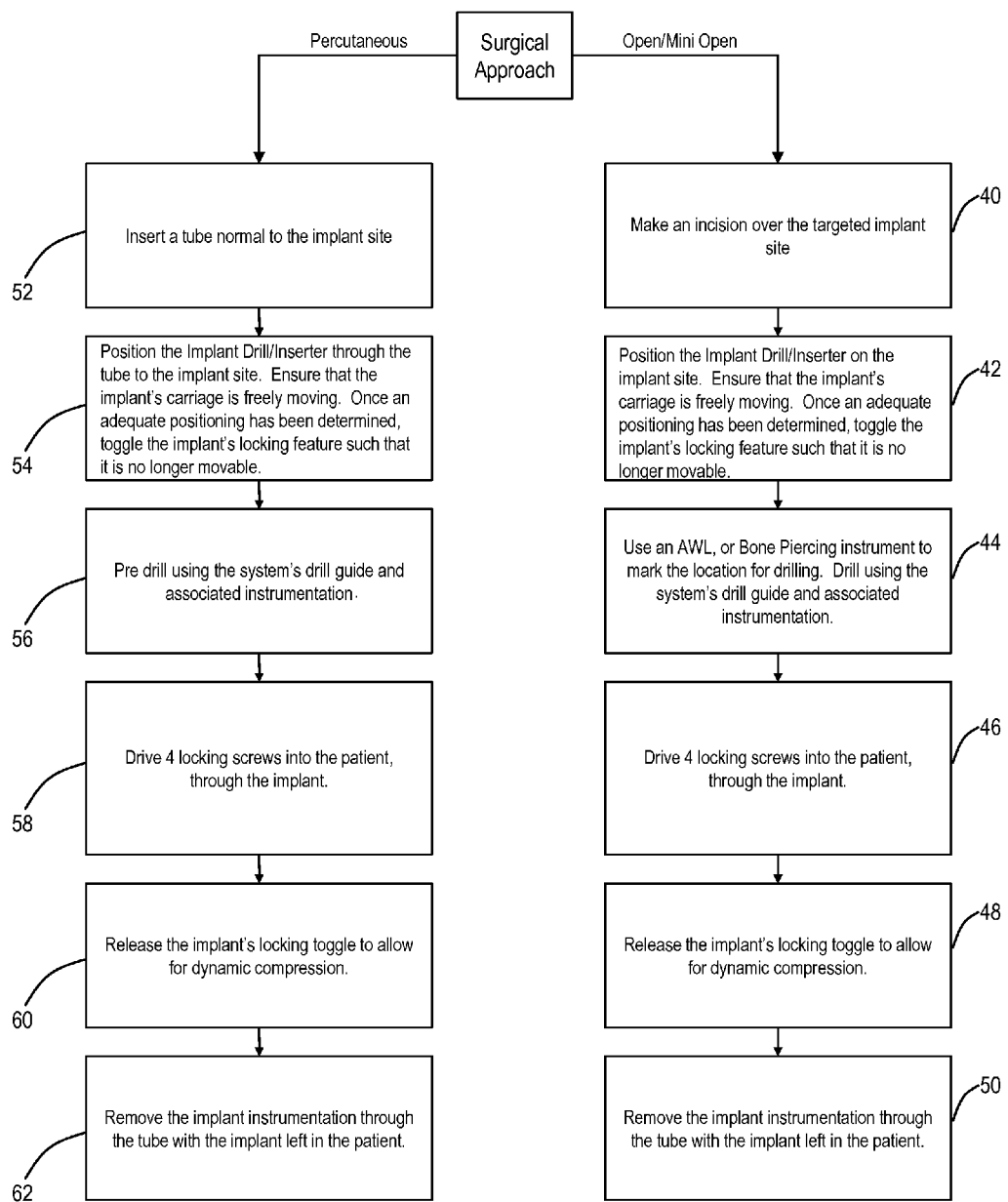
FIG. 9 is a flowchart illustrating exemplary embodiments of percutaneous and open surgical procedures for implanting and using the bone plates of the present invention.

Referring now to FIG. 9, in one exemplary embodiment, the surgical approach used to implant the bone plate 10 (FIGS. 1-8) of the present invention is open. In this open approach, an incision is first made over the target implant site 40. Next, an implant drill/inserter is placed substantially perpendicular to the implant site and the implant is positioned 42. The surgeon also ensures that the implant's carriage assembly 22 (FIGS. 1-8) is freely moving. Once the positioning is adequately determined, the implant's locking feature is toggled, such that the carriage assembly 22 is no longer moveable. Next, an awl or other bone piercing instrument is used to mark a drilling location and the locking screw holes or the like are drilled using a drill guide and/or associated instrumentation 44. Next, the locking screws or the like are engaged with the various bony structures through the implant 46. Next, the implant's locking toggle is released to allow for dynamic compression 48. Finally, the implant instrumentation is removed and the implant is left in the patient 50.

Referring again to FIG. 9, in another exemplary embodiment, the surgical approach used to implant the bone plate 10 (FIGS. 1-8) of the present invention is percutaneous. In this percutaneous approach, a tube is first inserted substantially perpendicular to the target implant site 52. Next, an implant drill/inserter is placed substantially perpendicular to the implant site and the implant is positioned 54. The surgeon also ensures that the implant's carriage assembly 22 (FIGS. 1-8) is freely moving. Once the positioning is adequately determined, the implant's locking feature is toggled, such that the carriage assembly 22 is no longer moveable. Next, an awl or other bone piercing instrument is used to mark a drilling location and the locking screw holes or the like are drilled using a drill guide and/or associated instrumentation 56. Next, the locking screws or the like are engaged with the various bony structures through the implant 58. Next, the implant's locking toggle is released to allow for dynamic compression 60. Finally, the implant instrumentation is removed and the implant is left in the patient 62.

Optionally, static compression can be applied across the surgical site after the implant is placed by releasing the locking toggle, applying a compressive load, and subsequently locking the locking toggle to maintain the compressive load across the surgical site.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A bone plate incorporating a compression mechanism, comprising:

a plate structure defining a plurality of screw receiving plate holes and a plurality of screw receiving plate slots; and a carriage assembly defining a plurality of screw receiving carriage holes and engaging the plurality of screw receiving plate slots, wherein the carriage assembly translates axially with respect to the plate structure via the plurality of screw receiving plate slots, thereby providing the compression mechanism;

wherein the carriage assembly translates axially with respect to the plate structure, thereby changing the relative position of the plurality of screw receiving plate holes associated with the plate structure and the plurality of screw receiving carriage holes associated with the carriage assembly, without changing the axial length of the plate structure or the bone plate; and wherein the carriage assembly comprises a plurality of screw receiving carriage assembly stems and an elongate bridge member that joins the plurality of screw receiving carriage assembly stems, and wherein the elongate bridge member translates axially with respect to the plate structure within a recess manufactured into the plate structure.

2. The bone plate of claim 1, wherein the plurality of screw receiving carriage assembly stems receive and retain a plurality of screws that pass through the carriage assembly.

3. The bone plate of claim 1, wherein the plurality of screw receiving plate slots translatably receive the plurality of screw receiving carriage assembly stems.

4. The bone plate of claim 1, wherein the plurality of screw receiving carriage assembly stems are axially translated with respect to the plate structure in unison and in parallel with respect to one another.

5. The bone plate of claim 1, wherein the plurality of screw receiving carriage assembly stems prevent rotation of the carriage assembly with respect to the plate structure when the carriage assembly is translated with respect to the plate structure.

6. The bone plate of claim 1, wherein the carriage assembly translates axially with respect to the plate structure, thereby changing the relative position of a plurality of screws associated with the plate structure and a plurality of screws associated with the carriage assembly, without changing the axial length of the plate structure or the bone plate.

7. The bone plate of claim 1, wherein the bone plate provides for axial translation of the plate structure with respect to the carriage assembly in a laterally and rotationally constrained manner.

8. The bone plate of claim 1, wherein the bone plate provides dynamic compression between the plate structure and the carriage assembly.

9. A bone plate incorporating a compression mechanism, comprising:
   a plate structure defining a plurality of screw receiving plate holes and a plurality of screw receiving plate slots; and
   a carriage assembly defining a plurality of screw receiving carriage holes and engaging the plurality of screw receiving plate slots, wherein the carriage assembly translates axially with respect to the plate structure via the plurality of screw receiving plate slots, thereby providing the compression mechanism;
   wherein the plate structure receives a plurality of screws;
   wherein the carriage assembly receives a plurality of screws;
   wherein the engagement of the plate structure and the carriage assembly provides dynamic compression between the plate structure and the carriage assembly;
   wherein the carriage assembly translates axially with respect to the plate structure, thereby changing the relative position of the plurality of screw receiving plate holes associated with the plate structure and the plurality of screw receiving carriage holes associated with the carriage assembly, without changing the axial length of the plate structure or the bone plate; and
   wherein the carriage assembly comprises a plurality of screw receiving carriage assembly stems and an elongate bridge member that joins the plurality of screw receiving carriage assembly stems, and wherein the elongate bridge member translates axially with respect to the plate structure within a recess manufactured into the plate structure.

10. The bone plate of claim 9, wherein the plurality of screw receiving carriage assembly stems receive and retain the plurality of screws that pass through the carriage assembly.

11. The bone plate of claim 9, wherein the plurality of screw receiving plate slots translatably receive the plurality of screw receiving carriage assembly stems.

12. The bone plate of claim 9, wherein the plurality of screw receiving carriage assembly stems are axially translated with respect to the plate structure in unison and in parallel with respect to one another.

13. The bone plate of claim 9, wherein the plurality of screw receiving carriage assembly stems prevent rotation of the carriage assembly with respect to the plate structure when the carriage assembly is translated with respect to the plate structure.

14. The bone plate of claim 9, wherein the carriage assembly translates axially with respect to the plate structure, thereby changing the relative position of the plurality of screws associated with the plate structure and the plurality of screws associated with the carriage assembly, without changing the axial length of the plate structure or the bone plate.

15. The bone plate of claim 9, wherein the bone plate provides for axial translation of the plate structure with respect to the carriage assembly in a laterally and rotationally constrained manner.

16. A bone plate incorporating a compression mechanism, comprising:
   a plate structure defining a plurality of screw receiving plate holes and a plurality of screw receiving plate slots; and
   a carriage assembly defining a plurality of screw receiving carriage holes and engaging the plurality of screw receiving plate slots, wherein the carriage assembly translates axially with respect to the plate structure via the plurality of screw receiving plate slots, thereby providing the compression mechanism;
   wherein the plate structure receives a plurality of screws;
   wherein the carriage assembly receives a plurality of screws;
   wherein the carriage assembly is selectively secured to the plate structure;
   wherein the carriage assembly translates axially with respect to the plate structure, thereby changing the relative position of the plurality of screw receiving plate holes associated with the plate structure and the plurality of screw receiving carriage holes associated with the carriage assembly, without changing the axial length of the plate structure or the bone plate; and
   wherein the carriage assembly comprises a plurality of screw receiving carriage assembly stems and an elongate bridge member that joins the plurality of screw receiving carriage assembly stems, and wherein the elongate bridge member translates axially with respect to the plate structure within a recess manufactured into the plate structure.

17. The bone plate of claim 16, wherein when the carriage assembly is not secured to the plate structure dynamic compression is provided.

18. The bone plate of claim 17, wherein when the carriage assembly is secured to the plate structure static compression is provided.

\* \* \* \* \*